US010086055B2

(12) United States Patent
Wu (10) Patent No.: US 10,086,055 B2
(45) Date of Patent: Oct. 2, 2018

(54) ADHERENT CANCER CELL LINE EXPRESSING A HEMATOLOGICAL TUMOR ANTIGEN

(71) Applicants: ProMab Biotechnologies, Inc., Richmond, CA (US); Forevertek Biotechnology Co., Ltd., Changsha, Hunan (CN)

(72) Inventor: Lijun Wu, Albany, CA (US)

(73) Assignees: ProMab Biotechnologies, Inc., Richmond, CA (US); Forevertek Biotechnology Co., Ltd., Changsha (CN)

( * ) Notice: Subject to any disclaimer, the term of this patent is extended or adjusted under 35 U.S.C. 154(b) by 0 days.

(21) Appl. No.: 15/610,419

(22) Filed: May 31, 2017

(65) Prior Publication Data

US 2017/0348403 A1   Dec. 7, 2017

Related U.S. Application Data

(60) Provisional application No. 62/343,976, filed on Jun. 1, 2016.

(51) Int. Cl.
| | | |
|---|---|---|
| A61K 39/00 | (2006.01) | |
| C07K 14/47 | (2006.01) | |
| C12N 15/09 | (2006.01) | |
| C12N 15/85 | (2006.01) | |
| C12N 5/071 | (2010.01) | |
| G01N 33/49 | (2006.01) | |

(52) U.S. Cl.
CPC ...... A61K 39/0011 (2013.01); C07K 14/4748 (2013.01); C12N 5/0602 (2013.01); C12N 15/09 (2013.01); G01N 33/4915 (2013.01); A61K 2039/5152 (2013.01); A61K 2039/5154 (2013.01); A61K 2039/5156 (2013.01); C07K 2317/70 (2013.01); C12N 2015/8572 (2013.01); C12N 2510/02 (2013.01)

(58) Field of Classification Search
CPC ........ A61K 2039/5158; A61K 39/0011; A61K 2039/5156; A61K 2039/70; A61K 38/00; A61K 45/06; C07K 14/70596; C07K 14/7051; C07K 16/2803; C07K 16/2866; C07K 2317/24; C07K 2317/622; C07K 2319/00
USPC ..... 435/235.1, 320.1, 325; 424/184.1, 192.1, 424/93.7
See application file for complete search history.

(56) References Cited

U.S. PATENT DOCUMENTS

| | | | | |
|---|---|---|---|---|
| 6,111,093 A  * | 8/2000 | Seed | .................... | C07K 14/705 435/252.3 |
| 2016/0362472 A1* | 12/2016 | Bitter | ................. | C07K 16/2803 |
| 2017/0166622 A1* | 6/2017 | Baeuerle | ............ | C07K 14/7051 |

OTHER PUBLICATIONS

Yin et al 1995, Cancer Research 55:4922-4928.*
Greiner et al (2006, Blood 108:4109-4177.*
Liadi et al (2013, Visualized Experiments | 72 | e50058 | p. 1-5.*
Pitcher et al. Molecular Biology of the Cell, vol. 10, 677-691, Mar. 1999. (Year: 1999).*

* cited by examiner

Primary Examiner — Janet L Epps-Smith
(74) Attorney, Agent, or Firm — Perkins Coie LLP; Viola T. Kung (57) ABSTRACT

The present invention relates to a transduced cancer cell line stably expressing a leukemia tumor antigen, wherein the cancer cell line is cervical cancer cells, breast cancer cells, ovarian cancer cells, pancreatic cancer cells, lung cancer cells, or glioblastoma cells. The transduced adherent cell line of the present invention is useful for many pre-clinical applications such as real time cytotoxicity assay or to test the effects of CAR-T cells that target the tumor antigen. The present invention is exemplified by Hela cell line stably expressing CD19.

3 Claims, 4 Drawing Sheets
Specification includes a Sequence Listing.

ADHERENT CANCER CELL LINE EXPRESSING A HEMATOLOGICAL TUMOR ANTIGEN

This application claims the priority of U.S. Provisional Application No. 62/343,976, dated Jun. 1, 2016, which is incorporated herein by reference in its entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of May 15, 2017, and a size of 13.0 kilobytes. The Sequence Listing filed via EFS-Web is part of the specification and is hereby incorporated in its entirety by reference herein.

FIELD OF THE INVENTION

The present invention relates to Hela-CD19 cell line that stably express CD19 (cluster of differentiation 19), which is a marker of hematopoietic cancers.

BACKGROUND OF THE INVENTION

Hela cell line was derived from cervical cancer cells taken on Feb. 8, 1951 from Henrietta Lacks, who died of cancer on Oct. 4, 1951 [Ghorashian et al. Br J Haematol 2015, 169, 463-478.] The cell line was found to be remarkably durable and extensively used in scientific research.

CD19 is a marker of hematopoietic cancers. B-lymphocyte antigen CD19, also known as CD19 (cluster of differentiation 19), is a protein that in humans is encoded by the CD19 gene. It is found on the surface of B-cells and overexpressed in leukemia and lymphoma and effectively targeted with CD19-CAR-T cells (Kochenderfer et al., Blood 2013, 122, 4129-4139, Scherer et al., J Exp Med 1953, 97, 695-710). There are many other hematological cancer tumor antigens such as CD4, CD5, CD7, CD8, CD10, CD20, CD22, CD23, CD24, CD33, CD38, CD47, CD56, CD57, CD123, CD138, BCMA and other which can be overexpressed on cancer cell surfaces and can be targeted by target-specific-CAR-T cells.

DETAILED DESCRIPTION OF THE INVENTION

Definitions

As used herein, a "chimeric antigen receptor (CAR)" means a fused protein comprising an extracellular domain capable of binding to an antigen, a transmembrane domain derived from a polypeptide different from a polypeptide from which the extracellular domain is derived, and at least one intracellular domain. The "chimeric antigen receptor (CAR)" is sometimes called a "chimeric receptor", a "T-body", or a "chimeric immune receptor (CIR)." The "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell.

As used herein, a FLAG-tag, or FLAG octapeptide, or FLAG epitope, is a polypeptide protein tag that can be added to a protein using recombinant DNA technology, having the sequence motif DYKDDDDK (SEQ ID NO: 1). It can be fused to the C-terminus or the N-terminus of a protein, or inserted within a protein.

As used herein, a "domain" means one region in a polypeptide which is folded into a particular structure independently of other regions.

As used herein, a "single chain variable fragment (scFv)" means a single chain polypeptide derived from an antibody which retains the ability to bind to an antigen. An example of the scFv includes an antibody polypeptide which is formed by a recombinant DNA technique and in which Fv regions of immunoglobulin heavy chain (H chain) and light chain (L chain) fragments are linked via a spacer sequence. Various methods for preparing an scFv are known to a person skilled in the art.

As used herein, a "tumor antigen" means a biological molecule having antigenicity, expression of which causes cancer.

The present invention is directed to a transduced adherent cell line that stably expresses a leukemia tumor antigen; it is a solid tumor cell line expressing a hematopoietic cancer marker. The adherent cells suitable in the present invention include those that are negative for hematologic markers and are durable; for example, cervical cancer cells such as Hela, breast cancer cells such as MCF-7, ovarian cancer cells such as A1747, pancreatic cancer cells such as PANC-1, lung cancer cells such as A549, and glioblastoma cells such as U87 or other type of solid cancer (prostate, colon, lung). A preferred cell line is Hela.

The hematological tumor antigen that can be expressed in the transduced adherent cell line of the present invention include CD (Cluster of Differentiation)19, CD4, CD5, CD7, CD8, CD10, CD20, CD22, CD23, CD24, CD33, CD38, CD47, CD56, CD57, CD123, CD138, BCMA and other In one embodiment, the present invention is directed to a transduced Hela cell line that stably expresses CD19 (Hela-CD19). The Hela-CD19 cell line is greater than 90% positive, preferably greater than 95%, greater than 98%, or greater than 99%, for expressing CD19.

The transduced adherent cell line of the present invention is useful for many pre-clinical applications. In one embodiment, the transduced adherent cell line is useful for real time cytotoxicity assay with CD19-CAR-T cells, CD20-CAR-T cells, CD22-CAR-T cells, CD23-CAR-T cells, or CD24-CAR-T cells, or CD4, CD5, CD7, CD8, CD10, CD33, CD38, CD47, CD56, CD57, CD123, CD138, BCMA and other CAR-T cells targeting each specific tumor antigen.

The Hela-CD19 cell line can be used in xenograft mice studies to test the effect of CD19-CAR-T cells.

The transduced cell line of the present invention is a solid cancer cell line that allows to study tumor microenvironment and signaling of solid tumors in vivo. Because it is an adherent cell line, it allows to perform different assays such as RTCA (real time cytotoxicity assay) where adherent properties of cells are used for quantification. The transduced cell line expresses tumor markers of leukemia, which can be used to study targeting of leukemia markers and tumor antigens.

The following examples further illustrate the present invention. These examples are intended merely to be illustrative of the present invention and are not to be construed as being limiting.

EXAMPLES

Example 1. Lentiviral Vector Containing Human CD19

The nucleic acid sequence of human CD19 is shown in SEQ ID NO: 2, which starts with start codon, ATG and finishes with stop codon TGA. The NCI Accession number of human CD19 is NM_001770. This human CD19 was inserted into Xba I and EcoR I sites of lentiviral vector (Lenti CMV-MCS-EF1a-puro, obtained from Systems Bioscience).

Example 2. Generation of CD19-Encoding Lentivirus and Lentivirus Production

DNAs encoding CD19 cDNA were synthesized and subcloned into a third-generation lentiviral vector, Lenti CMV-MCS-EF1a-puro by Syno Biological (Beijing, China). All lentiviral constructs were sequenced in both directions to confirm the construct sequence and used for lentivirus production. Ten million growth-arrested HEK293FT cells (Thermo Fisher) were seeded into T75 flasks and cultured overnight, then transfected with the pPACKH1 Lentivector Packaging mix (System Biosciences, Palo Alto, Calif.) and 10 μg of each lentiviral vector using the CalPhos Transfection Kit (Takara, Mountain View, Calif.). The next day the medium was replaced with fresh medium, and 48 h later the lentivirus-containing medium was collected. The medium was cleared of cell debris by centrifugation at 2100 g for 30 min. The virus particles were collected by centrifugation at 112,000 g for 100 min, suspended in DMEM or AIM V medium, aliquoted and frozen at −80° C. The titers of the virus preparations were determined by quantitative RT-PCR using the Lenti-X qRT-PCR kit (Takara) according to the manufacturer's protocol and the 7900HT thermal cycler (Thermo Fisher). The lentiviral titers were >$1\times10^8$ pfu/ml.

Example 3. Transduction of Hela Cells with Lentivirus and Generation of Hela-CD19 Cells CD19-lentivirus of Example 2 were thawed on ice. To each well of $1\times10^6$ Hela cells, $5\times10^6$ CD19-lentivirus, and 2 μL/mL of media of Transplus (Alstem, Richmond, Calif.) (a final dilution of 1:500) were added. Cells were incubated for an additional 24 hr before repeating addition of lentivirus.

The Hela cells were transduced with lentiviral construct containing CD19 DNA, and puromycin was added to the medium to select stable Hela-CD19 cells. Puromycin was added 1 μg/ml to DMEM with 10% FBS medium, and fresh medium was changed with puromycin 1 μg/ml every 3 days.

Hela cells were then grown in the continued presence of fresh medium with puromycin for a period of 12-14 days. The stable clone of Hela-CD19 cells were isolated and grown until confluence. The expression of CD19 was confirmed by FACS analysis with CD19 antibody.

The Hela-CD19 stable cell line was deposited on Jun. 1, 2017 with American Type Culture Collection (ATCC) under ATCC deposit number PTA-124207, under the Budapest Treaty provisions.

Example 4. Preparing CAR-T Cells (CD19-ScFv-CD28-CD3Zeta)

Sequence of CD19-CD28-CD3 zeta was described in [Kochenderfer et al. *J Immunother* 2009, 32, 689-702]. CD19 scFv and CD28-transmembrane and activation domains and CD3 zeta were subcloned into a third-generation lentiviral vector, Lenti CMV-MCS-EF1a-puro by Syno Biological (Beijing, China). All CAR lentiviral constructs were sequenced in both directions to confirm CAR sequence and used for lentivirus production.

The lentiviruses were generated in 293T cells, titer was established by RT-PCR, and was used for transduction of T cells according to protocol described in Example 2 of Berahovich et al Front Biosci (Landmark Ed). 22:1644-1654 (2017).

CAR-T cells (CD19ScFv-CD28-CD3zeta) were generated similarly as described for Hela cells in Example 3, but without selection of stable cell clones. No puromycin treatment was performed to preserve higher cell number. The CAR-T were used for cytotoxicity assay (Example 5) with target Hela-CD19 cells.

Example 5. Cytotoxicity Assay (Real-Time ACEA)

The cytotoxicity was performed using ACEA machine according to manufacturer's protocol listed below.

Adherent target cells (HeLa or HeLa-CD19) were seeded into 96-well E-plates (Acea Biosciences, San Diego, Calif.) at $1\times10^4$ cells per well and monitored in culture overnight with the impedance-based real-time cell analysis (RTCA) iCELLigence system (Acea Biosciences). The next day, the medium was removed and replaced with AIM V-AlbuMAX medium containing 10% FBS±$1\times10^5$ effector cells (CAR-T cells or non-transduced T cells), in triplicate. The cells in the E-plates were monitored for another 2-3 days with the RTCA system, and impedance was plotted over time. Cytolysis was calculated as (impedance of target cells without effector cells−impedance of target cells with effector cells)×100/impedance of target cells without effector cells.

Example 6. Flow Cytometry Results to Detect Expression of CD19

To measure CAR expression, 0.5 million cells were suspended in 100 μl of buffer (PBS containing 0.5.% BSA) and incubated on ice with 1 μl of human serum (Jackson Immunoresearch, West Grove, Pa.) for 10 min. The anti-CD19-PE or its isotype control PE-labelled antibody were added, and the cells were incubated on ice for 30 min. The cells were rinsed with 3 ml of buffer, then suspended in buffer and acquired on a FACSCalibur (BD Biosciences).

Figure 1:
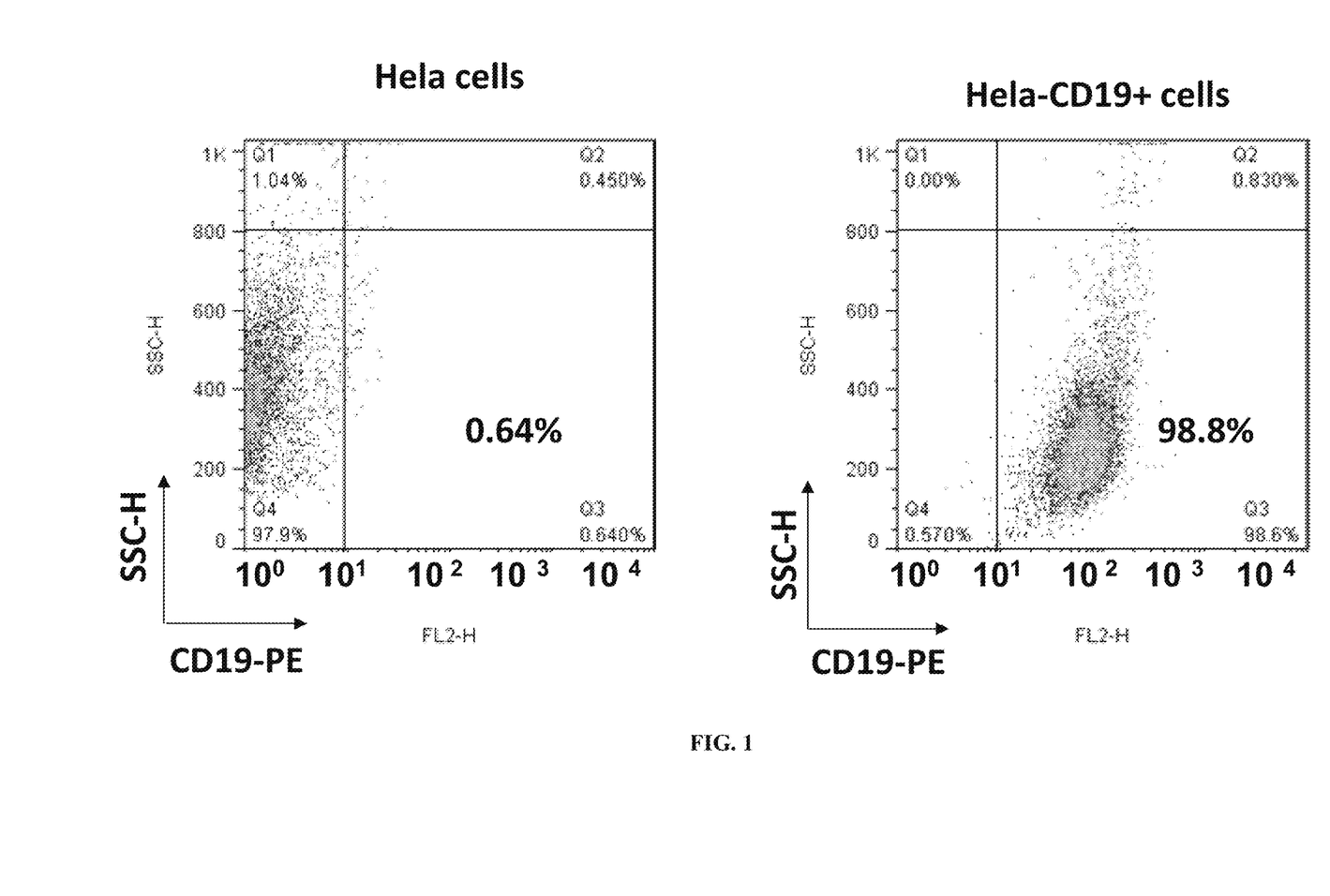
FIG. 1 shows the flow cytometry results of the expression of CD19 by Hela cells and Hela-CD19 cells.

Hela cells are negative for CD19. In Example 3, the Hela cells were stably transduced with CD19, and the resulting Hela-CD19 cells express CD19, as verified by flow cytometry with CD19-PE antibody (FIG. 1). The cells were almost 99% positive for CD19.

Example 7. Hela-CD19 Cells are Targeted by CD19-CAR-T and CD19/NK Cells In Vitro We used Hela-CD19 cells (Example 3), T cells, and CD19-CD28-CD3-zeta CAR-T (CD19scFv CAR-T, Example 4) cells in this Experiment.

Figure 2A:
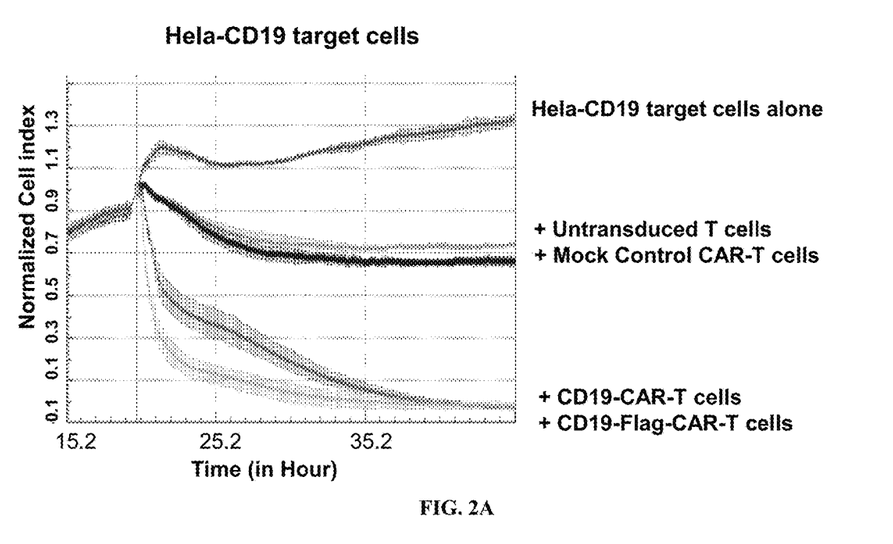
FIG. 2A shows CD19-CAR-T cells and CD19-FLAG-CAR-T cells effectively target Hela-CD19 line. Effector to target cells ratio is 5:1 in RTCA assay. Hela-CD19 cells are killed by CD19-CAR-T cells and CD19-FLAG-CAR-T cells.
Figure 2B:
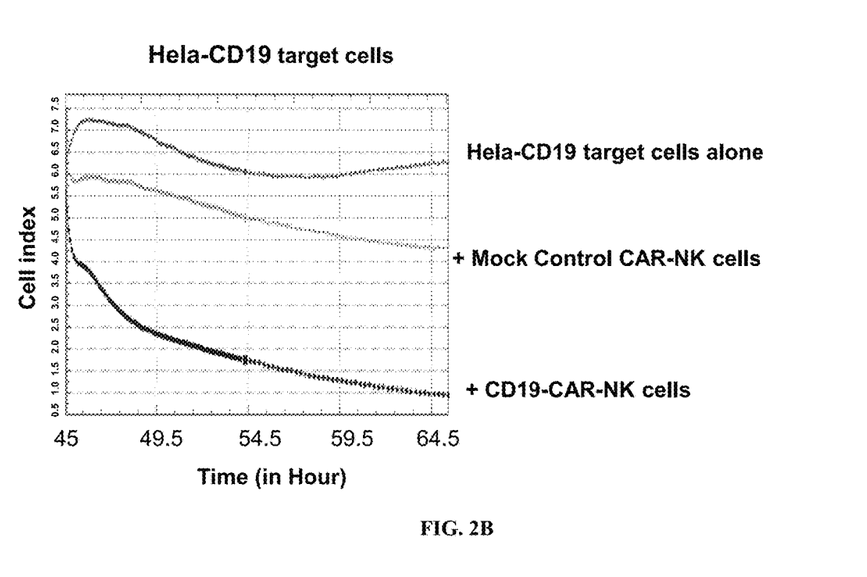
FIG. 2B shows CD19-CAR-NK cells effectively target Hela-CD19 line. NK, Natural Killer cells.

FIG. 2A shows real-time cytotoxicity assay with Hela-CD19 target cells and CD19-CAR-T effector cells. FIG. 2B shows real-time cytotoxicity assay with Hela-CD19 target cells and CD19-CAR effector NK cells.

FIG. 2A demonstrates that CD19-CAR-T cells effectively target Hela-CD19 line. The CD19-CAR-T cells were CD19-CD28-CD3 zeta, second generation CAR-T cells. Thus, Hela-CD19 can be used in cytotoxicity assays with CD19-CAR-T cells targeting CD19 antigen.

The same result was obtained with CD19-NK (natural killer) cells (FIG. 2B).

Example 8. Hela-CD19 Cells are Targeted by CD19-CAR-T Cells In Vivo

Figure 3:
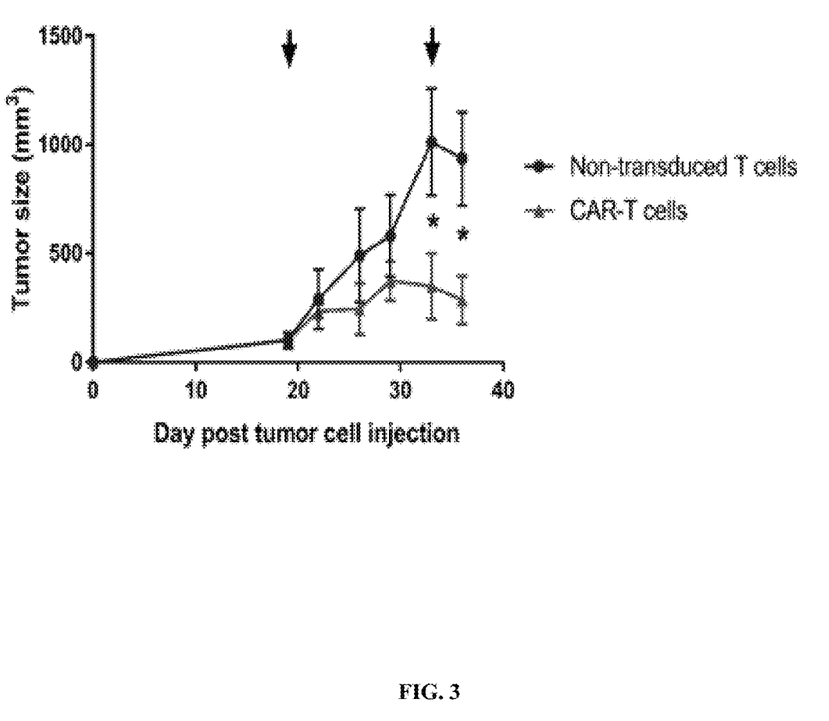
FIG. 3 shows that Hela-CD19 cervical cancer xenograft tumor growth was blocked by intratumoral injection of CD19-CAR-T cells. Intra-tumoral injections of CD19-CAR T cells and CD19-FLAG CAR-T cells significantly inhibited Hela-CD19 tumor growth. The growth curves are shown for the tumors treated with non-transduced T cells and the tumors treated with CD19 (day 19) and CD19-FLAG (day 33) CAR-T cells. *: $p<0.0.5$ for CAR-T cells compared to non-transduced T cells, determined by Student's t test assuming unequal variances.

To test that Hela-CD19 cells can be used with hematological cancer targets, we developed a novel xenograft tumor model using the HeLa-CD19 cell line. Immunodeficient NSG mice were injected subcutaneously on each flank with $2 \times 10^6$ HeLa-CD19 cells, and the sizes of the tumors were monitored for 36 days. The tumors injected intratumorally with CD19 and CD19-FLAG CAR-T cells (average 285 mm$^3$) were significantly smaller than the control tumors injected with non-transduced T cells (average 935 mm$^3$). FIG. 3 shows the average growth curves for the tumors treated with non-transduced T cells and the tumors treated with CD19 CAR-T cells on day 19 and CD19-FLAG CAR-T cells on day 33. The results show that intra-tumoral injections of CD19 and CD19-FLAG CAR-T cells significantly inhibited HeLa-CD19 tumor growth. *: $p<0.05$ for CAR-T cells compared to non-transduced T cells, determined by Student's t test assuming unequal variances.

Figure 4:
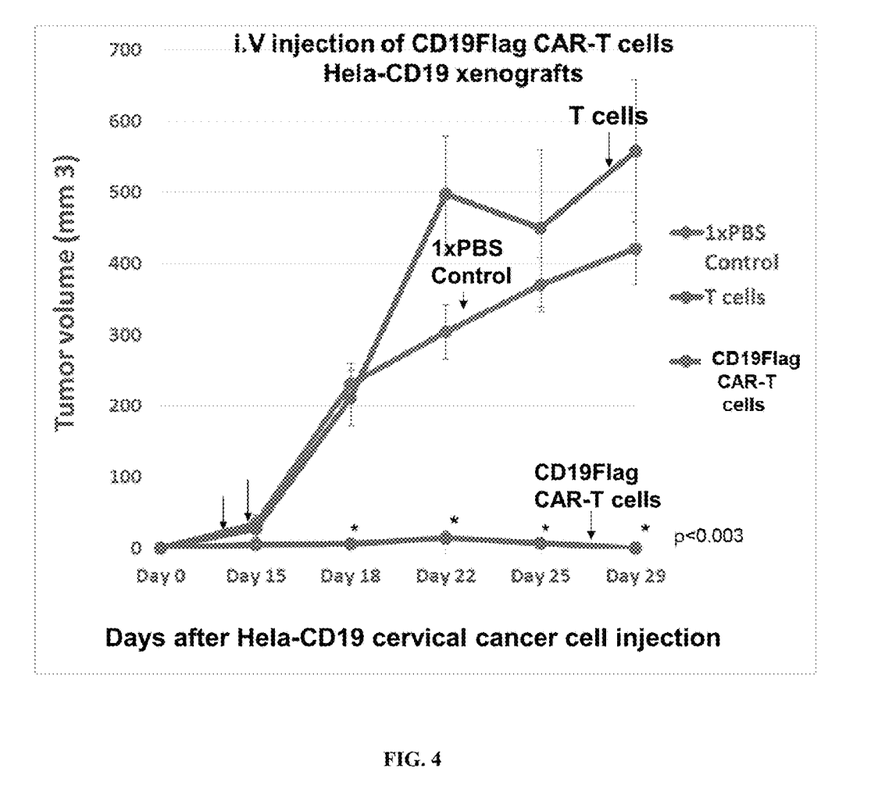
FIG. 4 shows that Hela-CD19 cervical cancer xenograft tumor growth was blocked by intravenous injection of CD19-FLAG CAR-T cells. Hela-CD19 xenograft tumor growth curves, averaged per group, *: $p<0.0.05$ for CD19-FLAG CAR-T cells compared to non-transduced T cells.

To characterize the effect of CD19-FLAG CAR-T cells in the HeLa-CD19 solid tumor model, a second study was conducted with earlier, intravenous application of the CD19-FLAG CAR-T cells. In this study, the CD19-FLAG CAR-T cells almost completely blocked tumor growth (see FIG. 4)

The results show that solid cancer Hela cell line with stably overexpressed leukemia antigen can be used as a model of solid cancer to study hematological targets in the solid tumor microenvironment allowing to study solid tumor biology, signaling and effect of hematological market targeting.

Example 9. CD20 Nucleotide Sequence

Examples 9-12 shows the nucleotide sequences of CD20, CD22, CD23, and CD24. The same approach as described above are used to generate solid tumor cell lines such as stable Hela or other stable cancer cell lines, which stably expressing these leukemia tumor antigens.

CD20 (Membrane-Spanning 4-Domains Subfamily A Member 1), nucleotide sequence is shown as SEQ ID NO: 4 (NCBI Accesion number, NM_021950.3),

Example 10. CD22 Nucleotide Sequence

CD22, nucleotide sequence is shown as SEQ ID NO: 5; Gen Bank Accession Number, X52785.1.

Example 11. CD23 Nucleotide Sequence

CD23 (other name: Fc Fragment Of IgE, Low Affinity II, Receptor For (CD23) is shown as SEQ ID NO: 6; Accesion number: AC008763.

Example 12. CD24 Nucleotide Sequence

CD24, (Accession NCBI number: NM_001291737.1 NM_001291738.1, NM_001291739.1, NM_013230.3, SEQ ID NO: 7

Example 13. Other Hematological Cancer Antigens Nucleotide and Amino-Acid Sequences CD4, CD5, CD7, CD8, CD10, CD33, CD38, CD47, CD56, CD57, CD123, CD138, BCMA and other nucleotide sequences are available from NCBI or Uniprot databases, respectively.

The same approach as described above are used to generate solid tumor cell lines such as stable Hela or other stable cancer cell lines, which stably expressing these leukemia tumor antigens.

It is to be understood that the foregoing describes preferred embodiments of the present invention and that modifications may be made therein without departing from the scope of the present invention as set forth in the claims.

What is claimed is:

1. A transduced cancer cell line, Hela, which is deposited under ATCC deposit number PTA-124207.

2. A method for measuring cytotoxicity of CD19-CAR T cells, comprising:
   seeding transduced Hela cancer cells that stably express CD19, having the ATCC deposit number PTA-12407, on a plate,
   adding CD19-CAR T cells to the plate, and
   measuring real time cytotoxicity of the CD19-CAR T cells.

3. The method of claim 2, wherein the CAR comprises CD19 scFv, CD28-transmembrane domain, CD28 activation domain, and CD3 zeta.

* * * * *

SEQUENCE LISTING

```
<160> NUMBER OF SEQ ID NOS: 7

<210> SEQ ID NO 1
<211> LENGTH: 8
<212> TYPE: PRT
<213> ORGANISM: Artificial Sequence
<220> FEATURE:
<223> OTHER INFORMATION: synthetic

<400> SEQUENCE: 1

Asp Tyr Lys Asp Asp Asp Asp Lys
1               5
```

<210> SEQ ID NO 2
<211> LENGTH: 1671
<212> TYPE: DNA
<213> ORGANISM: Homo sapiens

<400> SEQUENCE: 2

| | | | | | |
|---|---|---|---|---|---|
| atgccacctc | ctcgcctcct | cttcttcctc | ctcttcctca | cccccatgga | agtcaggccc | 60 |
| gaggaacctc | tagtggtgaa | ggtggaagag | ggagataacg | ctgtgctgca | gtgcctcaag | 120 |
| gggacctcag | atggccccac | tcagcagctg | acctggtctc | gggagtcccc | gcttaaaccc | 180 |
| ttcttaaaac | tcagcctggg | gctgccaggc | ctgggaatcc | acatgaggcc | cctggccatc | 240 |
| tggcttttca | tcttcaacgt | ctctcaacag | atgggggggct | tctacctgtg | ccagccgggg | 300 |
| cccccctctg | agaaggcctg | gcagcctggc | tggacagtca | atgtggaggg | cagcggggag | 360 |
| ctgttccggt | ggaatgtttc | ggacctaggt | ggcctgggct | gtggcctgaa | gaacaggtcc | 420 |
| tcagagggcc | ccagctcccc | ttccgggaag | ctcatgagcc | caagctgta | tgtgtgggcc | 480 |
| aaagaccgcc | ctgagatctg | ggaggagag | cctccgtgtg | tcccaccgag | ggacagcctg | 540 |
| aaccagagcc | tcagccagga | cctcaccatg | gcccctggct | ccacactctg | gctgtcctgt | 600 |
| ggggtacccc | ctgactctgt | gtccagggc | cccctctcct | ggacccatgt | gcaccccaag | 660 |
| gggcctaagt | cattgctgag | cctagagctg | aaggacgatc | gcccggccag | agatatgtgg | 720 |
| gtaatggaga | cgggtctgtt | gttgccccgg | gccacagctc | aagacgctgg | aaagtattat | 780 |
| tgtcaccgtg | caacctgac | catgtcattc | cacctggaga | tcactgctcg | gccagtacta | 840 |
| tggcactggc | tgctgaggac | tggtggctgg | aaggtctcag | ctgtgacttt | ggcttatctg | 900 |
| atcttctgcc | tgtgttccct | tgtgggcatt | cttcatcttc | aaagagccct | ggtcctgagg | 960 |
| aggaaaagaa | agcgaatgac | tgaccccacc | aggagattct | tcaaagtgac | gcctcccca | 1020 |
| ggaagcgggc | cccagaacca | gtacgggaac | gtgctgtctc | tccccacacc | cacctcaggc | 1080 |
| ctcggacgcg | cccagcgttg | gccgcaggc | ctggggggca | ctgccccgtc | ttatggaaac | 1140 |
| ccgagcagcg | acgtccaggc | ggatggagcc | ttggggtccc | ggagcccgcc | gggagtgggc | 1200 |
| ccagaagaag | aggaagggga | gggctatgag | gaacctgaca | gtgaggagga | ctccgagttc | 1260 |
| tatgagaacg | actccaacct | ggggcaggac | cagctctccc | aggatggcag | cggctacgag | 1320 |
| aaccctgagg | atgagcccct | gggtcctgag | gatgaagact | ccttctccaa | cgctgagtct | 1380 |
| tatgagaacg | aggatgaaga | gctgacccag | ccggtcgcca | ggacaatgga | cttcctgagc | 1440 |
| cctcatgggt | cagcctggga | ccccagccgg | gaagcaacct | ccctggggtc | ccagtcctat | 1500 |
| gaggatatga | gaggaatcct | gtatgcagcc | ccccagctcc | gctccattcg | gggccagcct | 1560 |
| ggacccaatc | atgaggaaga | tgcagactct | tatgagaaca | tggataatcc | cgatgggcca | 1620 |
| gacccagcct | ggggaggagg | gggccgcatg | ggcacctgga | gcaccaggtg | a | 1671 |

<210> SEQ ID NO 3
<211> LENGTH: 556
<212> TYPE: PRT
<213> ORGANISM: Homo sapiens

<400> SEQUENCE: 3

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln

```
                35                  40                  45
Gln Leu Thr Trp Ser Arg Glu Ser Pro Leu Lys Pro Phe Leu Lys Leu
 50                  55                  60
Ser Leu Gly Leu Pro Gly Leu Gly Ile His Met Arg Pro Leu Ala Ile
 65                  70                  75                  80
Trp Leu Phe Ile Phe Asn Val Ser Gln Gln Met Gly Gly Phe Tyr Leu
                 85                  90                  95
Cys Gln Pro Gly Pro Pro Ser Glu Lys Ala Trp Gln Pro Gly Trp Thr
                100                 105                 110
Val Asn Val Glu Gly Ser Gly Glu Leu Phe Arg Trp Asn Val Ser Asp
                115                 120                 125
Leu Gly Gly Leu Gly Cys Gly Leu Lys Asn Arg Ser Ser Glu Gly Pro
                130                 135                 140
Ser Ser Pro Ser Gly Lys Leu Met Ser Pro Lys Leu Tyr Val Trp Ala
145                 150                 155                 160
Lys Asp Arg Pro Glu Ile Trp Glu Gly Glu Pro Pro Cys Val Pro Pro
                165                 170                 175
Arg Asp Ser Leu Asn Gln Ser Leu Ser Gln Asp Leu Thr Met Ala Pro
                180                 185                 190
Gly Ser Thr Leu Trp Leu Ser Cys Gly Val Pro Pro Asp Ser Val Ser
                195                 200                 205
Arg Gly Pro Leu Ser Trp Thr His Val His Pro Lys Gly Pro Lys Ser
                210                 215                 220
Leu Leu Ser Leu Glu Leu Lys Asp Asp Arg Pro Ala Arg Asp Met Trp
225                 230                 235                 240
Val Met Glu Thr Gly Leu Leu Leu Pro Arg Ala Thr Ala Gln Asp Ala
                245                 250                 255
Gly Lys Tyr Tyr Cys His Arg Gly Asn Leu Thr Met Ser Phe His Leu
                260                 265                 270
Glu Ile Thr Ala Arg Pro Val Leu Trp His Trp Leu Leu Arg Thr Gly
                275                 280                 285
Gly Trp Lys Val Ser Ala Val Thr Leu Ala Tyr Leu Ile Phe Cys Leu
                290                 295                 300
Cys Ser Leu Val Gly Ile Leu His Leu Gln Arg Ala Leu Val Leu Arg
305                 310                 315                 320
Arg Lys Arg Lys Arg Met Thr Asp Pro Thr Arg Arg Phe Phe Lys Val
                325                 330                 335
Thr Pro Pro Pro Gly Ser Gly Pro Gln Asn Gln Tyr Gly Asn Val Leu
                340                 345                 350
Ser Leu Pro Thr Pro Thr Ser Gly Leu Gly Arg Ala Gln Arg Trp Ala
                355                 360                 365
Ala Gly Leu Gly Gly Thr Ala Pro Ser Tyr Gly Asn Pro Ser Ser Asp
                370                 375                 380
Val Gln Ala Asp Gly Ala Leu Gly Ser Arg Ser Pro Pro Gly Val Gly
385                 390                 395                 400
Pro Glu Glu Glu Glu Gly Glu Gly Tyr Glu Glu Pro Asp Ser Glu Glu
                405                 410                 415
Asp Ser Glu Phe Tyr Glu Asn Asp Ser Asn Leu Gly Gln Asp Gln Leu
                420                 425                 430
Ser Gln Asp Gly Ser Gly Tyr Glu Asn Pro Glu Asp Glu Pro Leu Gly
                435                 440                 445
Pro Glu Asp Glu Asp Ser Phe Ser Asn Ala Glu Ser Tyr Glu Asn Glu
                450                 455                 460
```

```
Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
            485                 490                 495

Ser Gln Ser Tyr Glu Asp Met Arg Gly Ile Leu Tyr Ala Pro Gln
            500                 505                 510

Leu Arg Ser Ile Arg Gly Gln Pro Gly Pro Asn His Glu Glu Asp Ala
            515                 520                 525

Asp Ser Tyr Glu Asn Met Asp Asn Pro Asp Gly Pro Asp Pro Ala Trp
            530                 535                 540

Gly Gly Gly Gly Arg Met Gly Thr Trp Ser Thr Arg
545                 550                 555

<210> SEQ ID NO 4
<211> LENGTH: 894
<212> TYPE: DNA
<213> ORGANISM: Homo sapiens

<400> SEQUENCE: 4
atgacaacac ccagaaattc agtaaatggg actttcccgg cagagccaat gaaaggccct      60
attgctatgc aatctggtcc aaaaccactc ttcaggagga tgtcttcact ggtgggcccc     120
acgcaaagct tcttcatgag ggaatctaag actttggggg ctgtccagat tatgaatggg     180
ctcttccaca ttgccctggg ggtcttctg atgatcccag cagggatcta tgcacccatc      240
tgtgtgactg tgtggtaccc tctctgggga ggcattatgt atattatttc cggatcactc     300
ctggcagcaa cggagaaaaa ctccaggaag tgtttggtca aggaaaaat gataatgaat      360 tcattgagcc tctttgctgc catttctgga atgattcttt caatcatgga catacttaat     420
attaaaattt cccattttt aaaaatggag agtctgaatt ttattagagc tcacacacca     480
tatattaaca tatacaactg tgaaccagct aatccctctg agaaaaactc cccatctacc     540
caatactgtt acagcataca atctctgttc ttgggcattt tgtcagtgat gctgatcttt     600
gccttcttcc aggaacttgt aatagctggc atcgttgaga tgaatgaa agaacgtgc       660 tccagaccca atctaacat agttctcctg tcagcagaag aaaaaaaaga acagactatt     720
gaaataaaag aagaagtggt tgggctaact gaaacatctt cccaaccaaa gaatgaagaa    780
gacattgaaa ttattccaat ccaagaagag aagaagaag aaacagagac gaactttcca    840
gaacctcccc aagatcagga atcctcacca atagaaaatg acagctctcc ttaa          894

<210> SEQ ID NO 5
<211> LENGTH: 1944
<212> TYPE: DNA
<213> ORGANISM: Homo sapiens

<400> SEQUENCE: 5
atgcatctcc tcggcccctg gctcctgctc ctggttctag aatacttggc tttctctgac      60
tcaagtaaat gggttttttga gcaccctgaa accctctacg cctgggaggg ggcctgcgtc    120
tggatcccct gcacctacag agccctagat ggtgacctgg aaagcttcat cctgttccac    180
aatcctgagt ataacaagaa cacctcgaag tttgatggga agactcta tgaaagcaca     240 aaggatggga aggttccttc tgagcagaaa agggtgcaat tcctgggaga caagaataag    300
aactgcacac tgagtatcca cccggtgcac ctcaatgaca gtggtcagct ggggctgagg    360
atggagtcca gactgagaa atggatggaa cgaatacacc tcaatgtctc tgaaaggcct    420
```

```
tttccacctc atatccagct ccctccagaa attcaagagt cccaggaagt cactctgacc      480
tgcttgctga atttctcctg ctatgggtat ccgatccaat tgcagtggct cctagagggg      540
gttccaatga ggcaggctgc tgtcacctcg acctccttga ccatcaagtc tgtcttcacc      600
cggagcgagc tcaagttctc cccacagtgg agtcaccatg gaagattgtg acctgccag      660 cttcaggatg cagatgggaa gttcctctcc aatgacacgg tgcagctgaa cgtgaagcat      720
cctcccaaga aggtgaccac agtgattcaa aaccccatgc cgattcgaga aggagacaca      780 gtgaccctttt cctgtaacta caattccagt aaccccagtg ttacccggta tgaatggaaa      840
ccccatggcg cctgggagga gccatcgctt ggggtgctga agatccaaaa cgttggctgg      900
gacaacacaa ccatcgcctg cgcagcttgt aatagttggt gctcgtgggc ctccctgtc       960 gccctgaatg tccagtatgc cccccgagac gtgagggtcc ggaaaatcaa gcccctttcc     1020
gagattcact ctggaaactc ggtcagcctc caatgtgact tctcaagcag ccaccccaaa     1080
gaagtccagt tcttctggga gaaaaatggc aggcttctgg ggaaagaaag ccagctgaat     1140
tttgactcca tctccccaga agatgctggg agttacagct gctgggtgaa caactccata     1200
ggacagacag cgtccaaggc ctggacactt gaagtgctgt atgcacccag gaggctgcgt     1260
gtgtccatga gcccgggggga ccaagtgatg gaggggaaga gtgcaaccct gacctgtgag     1320
agcgacgcca accctcccgt ctcccactac acctggtttg actggaataa ccaaagcctc     1380
ccctaccaca gccagaagct gagattggag ccggtgaagg tccagcactc gggtgcctac     1440
tggtgccagg ggaccaacag tgtgggcaag ggccgttcgc ctctcagcac cctcaccgtc     1500
tactatagcc cggagaccat cggcaggcga gtggctgtgg gactcgggtc ctgcctcgcc     1560
atcctcatcc tggcaatctg tgggctcaag ctccagcgac gttggaagag gacacagagc     1620 cagcagggggc ttcaggagaa ttccagcggc cagagcttct tgtgtgaggaa taaaaaggtt     1680 agaagggccc ccctctctga aggcccccac tccctgggat gctacaatcc aatgatggaa     1740
gatggcatta gctacaccac cctgcgcttt cccgagatga acataccacg aactggagat     1800
gcagagtcct cagagatgca gagacctccc ccggactgcg atgacacggt cacttattca     1860
gcattgcaca agcgccaagt gggcactatg agaacgtcat ccagatttt ccagaagatg     1920 agggggattca ttactcagag ctga                                           1944
```

<210> SEQ ID NO 6
<211> LENGTH: 972
<212> TYPE: DNA
<213> ORGANISM: Homo sapiens

<400> SEQUENCE: 6

```
atggaggaag gtcaatattc agagatcgag gagcttccca ggaggcggtg ttgcaggcgt       60
gggactcaga tcgtgctgct ggggctggtg accgccgctc tgtgggctgg gctgctgact      120
ctgcttctcc tgtggcactg gacaccacac cagagtctaa aacagctgga agagagggct      180 gccccggaacg tctctcaagt ttccaagaac ttggaaagcc accacggtga ccagatggcg      240
cagaaatccc agtccacgca gatttcacag gaactggagg aacttcgagc tgaacagcag      300
agattgaaat ctcaggactt ggagctgtcc tggaacctga cgggcttca agcagatctg      360 agcagcttca gtcccagga attgaacgag aggaacgaag cttcagattt gctggaaaga      420 ctccggggagg aggtgacaaa gctaaggatg gagttgcagg tgtccagcgg ctttgtgtgc      480
aacacgtgcc ctgaaaagtg gatcaatttc caacggaagt gctactactt cggcaagggc      540
accaagcagt gggtccacgc ccggtatgcc tgtgacgaca tggaagggca gctggtcagc      600
```

```
atccacagcc cggaggagca ggacttcctg accaagcatg ccagccacac cggctcctgg    660
attggccttc ggaacttgga cctgaagggg gagtttatct gggtggatgg gagccacgtg    720
gactacagca actgggctcc aggggagccc accagccgga gccagggcga ggactgcgtg    780
atgatgcggg gctccggtcg ctggaacgac gccttctgcg accgtaagct gggcgcctgg    840
gtgtgcgacc ggctggccac atgcacgccg ccagccagcg aaggttccgc ggagtccatg    900
ggacctgatt caagaccaga ccctgacggc cgcctgccca ccccctctgc ccctctccac    960
tcttgagcat gg                                                         972

<210> SEQ ID NO 7
<211> LENGTH: 243
<212> TYPE: DNA
<213> ORGANISM: Homo sapiens

<400> SEQUENCE: 7
atgggcagag caatggtggc caggctcggg ctggggctgc tgctgctggc actgctccta     60
cccacgcaga tttattccag tgaaacaaca actggaactt caagtaactc ctcccagagt    120
acttccaact ctgggttggc cccaaatcca actaatgcca ccaccaaggc ggctggtggt    180
gccctgcagt caacagccag tctcttcgtg gtctcactct ctcttctgca tctctactct    240
tag                                                                   243
```